(12) United States Patent
Shellenberger

(10) Patent No.: US 12,102,334 B2
(45) Date of Patent: Oct. 1, 2024

(54) CLIP APPLIER WITH STABILIZING MEMBER

(71) Applicant: TELEFLEX MEDICAL INCORPORATED, Morrisville, NC (US)

(72) Inventor: Carson J. Shellenberger, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 66 days.

(21) Appl. No.: 17/516,634

(22) Filed: Nov. 1, 2021

(65) Prior Publication Data

US 2022/0047271 A1  Feb. 17, 2022

Related U.S. Application Data

(63) Continuation of application No. 15/927,408, filed on Mar. 21, 2018, now Pat. No. 11,160,559.
(Continued)

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/1222* (2013.01);
(Continued)

(58) Field of Classification Search
CPC ............ A61B 17/0682; A61B 17/0644; A61B 17/083; A61B 17/105; A61B 17/10;
(Continued)

(56) References Cited

U.S. PATENT DOCUMENTS

| 929,868 A | 8/1909 | Mueller |
| 1,482,290 A | 1/1924 | Elzi |

(Continued)

FOREIGN PATENT DOCUMENTS

| AU | 676836 B2 | 3/1997 |
| CN | 1356092 A | 7/2002 |

(Continued)

*Primary Examiner* — Martin T Ton
(74) *Attorney, Agent, or Firm* — BakerHostetler

(57) ABSTRACT

A clip applier may be configured to apply a surgical clip to tissue. The clip applier may include a first jaw member, a second jaw member, and a stabilizing member, each configured to engage the surgical clip. The stabilizing member may be configured to move longitudinally with respect to the clip applier from a first position at least partially between the first and second jaw members to a second position at least partially between the first and second jaw members. The longitudinal movement of the stabilizing member may be constrained to longitudinal movement between the first and second positions. The stabilizing member may include first and second sidewalls on a distal portion, where the first and second sidewalls are configured to stabilize the surgical clip in a lateral direction. The clip applier may include a hinge pin received in a longitudinal channel of the stabilizing member.

19 Claims, 4 Drawing Sheets

Related U.S. Application Data

(60) Provisional application No. 62/474,523, filed on Mar. 21, 2017.

(51) Int. Cl.
  *A61B 17/00* (2006.01)
  *A61B 17/28* (2006.01)
  *A61B 17/29* (2006.01)

(52) U.S. Cl.
  CPC .................. *A61B 17/1227* (2013.01); *A61B 2017/00296* (2013.01); *A61B 17/282* (2013.01); *A61B 2017/2926* (2013.01)

(58) Field of Classification Search
  CPC ... A61B 17/12; A61B 17/122; A61B 17/1222; A61B 17/1227; A61B 17/128; A61B 17/1285; A61B 2017/12004; A61B 2017/1225
  See application file for complete search history.

(56) References Cited

U.S. PATENT DOCUMENTS

| | | |
|---|---|---|
| 1,728,322 A | 9/1929 | Badrian |
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Bay |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,446,212 A | 5/1969 | Le Roy |
| 3,463,156 A | 8/1969 | Mcdermott et al. |
| 3,503,396 A | 3/1970 | Pierie et al. |
| 3,503,397 A | 3/1970 | Fogarty et al. |
| 3,503,398 A | 3/1970 | Fogarty et al. |
| 3,766,925 A | 10/1973 | Rubricius |
| 3,825,012 A | 7/1974 | Nicoll |
| 3,827,438 A | 8/1974 | Kees |
| 3,867,944 A | 2/1975 | Samuels |
| 3,874,042 A | 4/1975 | Eddleman et al. |
| 3,954,108 A | 5/1976 | Davis |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,344,531 A | 8/1982 | Giersch |
| 4,345,600 A | 8/1982 | Rothfuss |
| 4,346,869 A | 8/1982 | Macneill |
| 4,390,019 A | 6/1983 | Leveen et al. |
| 4,394,864 A * | 7/1983 | Sandhaus ............... A61F 6/204 606/221 |
| 4,414,721 A | 11/1983 | Hufnagel |
| 4,418,694 A | 12/1983 | Beroff et al. |
| 4,428,374 A | 1/1984 | Auburn |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di et al. |
| 4,492,232 A | 1/1985 | Green |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A | 10/1986 | Golden |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A | 10/1991 | Schmidt et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | Van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | Mcquilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,700,270 A | 12/1997 | Peyser et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,797,922 A | 8/1998 | Hessel et al. |
| 5,810,853 A | 9/1998 | Yoon |
| 5,833,696 A | 11/1998 | Whitfield et al. |
| 5,843,097 A | 12/1998 | Mayenberger et al. |

(56) References Cited

U.S. PATENT DOCUMENTS

| | | |
|---|---|---|
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,997,548 A | 12/1999 | Jahanger |
| 6,010,516 A | 1/2000 | Hulka |
| 6,013,088 A | 1/2000 | Karavidas |
| 6,015,417 A | 1/2000 | Reynolds, Jr. |
| 6,050,996 A | 4/2000 | Schmaltz et al. |
| 6,131,576 A | 10/2000 | Davis |
| 6,158,583 A | 12/2000 | Forster |
| 6,210,419 B1 | 4/2001 | Mayenberger et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,253 B1 | 8/2001 | Forster et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,558,408 B1 | 5/2003 | Fogarty et al. |
| 6,599,298 B1 * | 7/2003 | Forster .......... A61B 17/128 606/139 |
| 6,695,854 B1 | 2/2004 | Kayan et al. |
| 6,699,258 B1 | 3/2004 | Sadler et al. |
| 6,719,766 B1 | 4/2004 | Buelna et al. |
| 6,773,438 B1 | 8/2004 | Knodel et al. |
| 6,780,195 B2 | 8/2004 | Porat |
| 6,814,742 B2 | 11/2004 | Kimura et al. |
| 6,824,547 B2 | 11/2004 | Wilson et al. |
| 6,837,895 B2 | 1/2005 | Mayenberger |
| 6,843,253 B2 | 1/2005 | Parkes |
| 6,863,675 B2 | 3/2005 | Wilson, Jr. |
| 6,880,699 B2 | 4/2005 | Gallagher |
| 6,926,712 B2 | 8/2005 | Phan |
| 6,932,816 B2 | 8/2005 | Phan |
| 6,989,017 B2 | 1/2006 | Howell et al. |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,131,977 B2 | 11/2006 | Fowler |
| 7,179,265 B2 | 2/2007 | Manetakis et al. |
| 7,211,091 B2 | 5/2007 | Fowler et al. |
| 7,211,092 B2 | 5/2007 | Hughett |
| 7,261,724 B2 | 8/2007 | Molitor et al. |
| 7,316,696 B2 | 1/2008 | Wilson et al. |
| 7,326,223 B2 | 2/2008 | Wilson, Jr. |
| 7,329,266 B2 | 2/2008 | Royse et al. |
| 7,357,805 B2 | 4/2008 | Masuda et al. |
| 7,402,164 B2 | 7/2008 | Watson et al. |
| 7,572,266 B2 | 8/2009 | Young et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,648,514 B1 * | 1/2010 | Nakao .......... A61B 17/064 606/151 |
| 7,727,231 B2 | 6/2010 | Swanson |
| 7,753,908 B2 | 7/2010 | Swanson |
| 7,785,324 B2 | 8/2010 | Eberl |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,142,451 B2 | 3/2012 | Boulnois et al. |
| 8,262,639 B2 | 9/2012 | Mathias |
| 8,403,138 B2 | 3/2013 | Weisshaupt et al. |
| 8,425,412 B2 | 4/2013 | Rucker |
| 8,465,507 B2 | 6/2013 | Cosgrove et al. |
| 8,512,357 B2 | 8/2013 | Viola |
| 8,585,718 B2 | 11/2013 | Disch et al. |
| 8,764,774 B2 | 7/2014 | Sigmon, Jr. |
| 8,839,954 B2 | 9/2014 | Disch |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,737,309 B1 | 8/2017 | Ad |
| 9,775,635 B2 | 10/2017 | Takei |
| 9,855,053 B2 | 1/2018 | Bagaoisan et al. |
| 9,901,352 B2 | 2/2018 | Fago et al. |
| 9,955,977 B2 | 5/2018 | Martinez et al. |
| 10,064,623 B2 | 9/2018 | Soutorine et al. |
| 10,136,898 B2 | 11/2018 | Schmidt et al. |
| 10,285,712 B2 | 5/2019 | Cosgrove et al. |
| 10,292,712 B2 | 5/2019 | Shankarsetty |
| 10,307,166 B2 | 6/2019 | Willett et al. |
| 10,383,637 B2 | 8/2019 | Castro |
| 10,548,609 B2 | 2/2020 | Ramsey et al. |
| 10,758,243 B2 | 9/2020 | Salas |
| 10,925,616 B2 | 2/2021 | Shellenberger et al. |
| 11,160,559 B2 | 11/2021 | Shellenberger |
| 11,266,408 B2 | 3/2022 | Shellenberger |
| 11,534,177 B2 | 12/2022 | Shellenberger et al. |
| 11,576,680 B2 | 2/2023 | Ramsey et al. |
| 11,607,227 B2 | 3/2023 | Shellenberger |
| 2002/0046961 A1 | 4/2002 | Levinson et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0014060 A1 | 1/2003 | Wilson et al. |
| 2003/0074009 A1 | 4/2003 | Ramsey et al. |
| 2003/0158548 A1 | 8/2003 | Phan et al. |
| 2004/0010272 A1 * | 1/2004 | Manetakis .......... A61B 17/1285 606/143 |
| 2004/0040875 A1 | 3/2004 | Gallagher |
| 2004/0044352 A1 | 3/2004 | Fowler et al. |
| 2004/0059359 A1 | 3/2004 | Wilson |
| 2004/0097970 A1 | 5/2004 | Hughett |
| 2004/0172043 A1 | 9/2004 | Watson et al. |
| 2005/0090838 A1 | 4/2005 | Sixto et al. |
| 2005/0149063 A1 | 7/2005 | Young et al. |
| 2005/0149068 A1 | 7/2005 | Williams et al. |
| 2005/0149069 A1 | 7/2005 | Bertolero et al. |
| 2005/0165421 A1 | 7/2005 | Wilson et al. |
| 2005/0165422 A1 | 7/2005 | Wilson, Jr. |
| 2005/0165423 A1 | 7/2005 | Gallagher et al. |
| 2005/0165429 A1 | 7/2005 | Douglas et al. |
| 2005/0171560 A1 | 8/2005 | Hughett |
| 2005/0234478 A1 | 10/2005 | Wixey et al. |
| 2005/0240219 A1 | 10/2005 | Kahle et al. |
| 2005/0277959 A1 | 12/2005 | Cosgrove et al. |
| 2006/0217749 A1 | 9/2006 | Wilson et al. |
| 2007/0016228 A1 | 1/2007 | Salas |
| 2007/0049947 A1 * | 3/2007 | Menn .......... A61B 17/10 606/142 |
| 2007/0083218 A1 | 4/2007 | A. Morris |
| 2007/0118161 A1 | 5/2007 | Kennedy et al. |
| 2007/0149989 A1 | 6/2007 | Santilli et al. |
| 2007/0276417 A1 | 11/2007 | Mendes et al. |
| 2007/0282355 A1 | 12/2007 | Brown et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0112233 A1 | 4/2009 | Xiao |
| 2009/0171380 A1 | 7/2009 | Whiting |
| 2009/0240266 A1 | 9/2009 | Dennis |

(56) References Cited

U.S. PATENT DOCUMENTS

| | | |
|---|---|---|
| 2010/0057107 A1 | 3/2010 | Sorrentino et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274262 A1 | 10/2010 | Schulz et al. |
| 2010/0274264 A1* | 10/2010 | Schulz ............... A61B 17/1285 606/143 |
| 2010/0274268 A1 | 10/2010 | Singh et al. |
| 2011/0022079 A1 | 1/2011 | Miles et al. |
| 2011/0087244 A1 | 4/2011 | Weisshaupt et al. |
| 2011/0144665 A1 | 6/2011 | Malkowski |
| 2011/0245848 A1 | 10/2011 | Rosenberg et al. |
| 2011/0295291 A1 | 12/2011 | Trivisani |
| 2012/0074200 A1 | 3/2012 | Schmid et al. |
| 2012/0083803 A1* | 4/2012 | Patel .................. A61B 17/1285 606/157 |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0253535 A1 | 9/2013 | Pribanic et al. |
| 2013/0261642 A1 | 10/2013 | Willett et al. |
| 2014/0018830 A1 | 1/2014 | Shelton, IV |
| 2014/0058411 A1 | 2/2014 | Soutorine et al. |
| 2014/0207156 A1 | 7/2014 | Malkowski |
| 2014/0243862 A1 | 8/2014 | Bagaoisan et al. |
| 2014/0309677 A1 | 10/2014 | Baldwin |
| 2015/0066057 A1 | 3/2015 | Malkowski et al. |
| 2015/0136835 A1 | 5/2015 | Shelton, IV et al. |
| 2015/0190137 A1 | 7/2015 | Salas |
| 2015/0320426 A1 | 11/2015 | Cosgrove et al. |
| 2016/0151073 A1 | 6/2016 | Castro et al. |
| 2016/0174981 A1 | 6/2016 | Fago et al. |
| 2016/0213377 A1 | 7/2016 | Shankarsetty |
| 2016/0256157 A1 | 9/2016 | Rockrohr et al. |
| 2016/0270790 A1 | 9/2016 | Jankowski |
| 2016/0354089 A1 | 12/2016 | Whiting |
| 2017/0014135 A1 | 1/2017 | Martin et al. |
| 2017/0238935 A1 | 8/2017 | Shi |
| 2018/0036008 A1 | 2/2018 | Ramsey et al. |
| 2018/0168659 A1 | 6/2018 | Bagaoisan et al. |
| 2018/0271527 A1 | 9/2018 | Shellenberger |
| 2018/0271532 A1 | 9/2018 | Shellenberger |
| 2018/0271534 A1 | 9/2018 | Shellenberger |
| 2018/0271535 A1 | 9/2018 | Shellenberger et al. |
| 2018/0271536 A1 | 9/2018 | Shellenberger et al. |
| 2021/0128159 A1 | 5/2021 | Taylor et al. |

FOREIGN PATENT DOCUMENTS

| | | |
|---|---|---|
| CN | 1846638 A | 10/2006 |
| CN | 101543418 A | 9/2009 |
| CN | 103181809 A | 7/2013 |
| CN | 103442658 A | 12/2013 |
| CN | 103930054 A | 7/2014 |
| CN | 104039248 A | 9/2014 |
| CN | 104367363 A | 2/2015 |
| CN | 104414701 A | 3/2015 |
| CN | 105054989 A | 11/2015 |
| CN | 105078536 A | 11/2015 |
| CN | 105816217 A | 8/2016 |
| CN | 106037947 A | 10/2016 |
| CN | 106264646 A | 1/2017 |
| CN | 110740696 A | 1/2020 |
| EP | 0086640 A2 | 8/1983 |
| EP | 0201344 A2 | 11/1986 |
| EP | 0314064 A2 | 5/1989 |
| EP | 0576835 A2 | 1/1994 |
| EP | 1233705 A2 | 8/2002 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 61-007818 B2 | 3/1986 |
| JP | 61-259652 A | 11/1986 |
| JP | 03-178648 A | 8/1991 |
| JP | 05-200039 A | 8/1993 |
| JP | 07-163574 A | 6/1995 |
| JP | 2002-345828 A | 12/2002 |
| JP | 2004-522468 A | 7/2004 |
| JP | 2004-535236 A | 11/2004 |
| JP | 4263594 B2 | 5/2009 |
| JP | 2011-036675 A | 2/2011 |
| JP | 2011-517423 A | 6/2011 |
| JP | 2014-531250 A | 11/2014 |
| JP | 2015-043977 A | 3/2015 |
| JP | 7329038 B2 | 8/2023 |
| WO | 97/38634 A1 | 10/1997 |
| WO | 01/35837 A1 | 5/2001 |
| WO | 01/37742 A2 | 5/2001 |
| WO | 2004/043225 A2 | 5/2004 |
| WO | 2005/107613 A1 | 11/2005 |
| WO | 2006/102578 A1 | 9/2006 |
| WO | 2012/075532 A1 | 6/2012 |
| WO | 2013/040467 A2 | 3/2013 |
| WO | 2015/099067 A1 | 7/2015 |
| WO | 2016/094647 A1 | 6/2016 |
| WO | 2018/027032 A1 | 2/2018 |
| WO | 2018/175626 A1 | 9/2018 |
| WO | 2020/018784 A1 | 1/2020 |

* cited by examiner

CLIP APPLIER WITH STABILIZING MEMBER

PRIORITY

This application is a continuation of U.S. application Ser. No. 15/927,408, filed Mar. 21, 2018, which claims the benefit of U.S. Provisional Patent Application No. 62/474,523, filed on Mar. 21, 2017, the entirety of each disclosure is incorporated herein by reference.

TECHNICAL FIELD

The present disclosure relates generally to clip appliers, and more particularly, to clip appliers with a stabilizing member biased into engagement with a surgical chip.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast surgical clips are relatively quick and easy to apply. Accordingly, the use of surgical clips in endoscopic and open surgical procedures has grown dramatically.

SUMMARY

The present inventor recognizes that there is a need to improve one or more features of the clip appliers and/or surgical clips, such as stability of the surgical clip in a clip applier. Surgical clips are often applied by clip appliers with a pair of opposing jaws. Currently available clip appliers often secure the clip with two points of contact, for example, the opposing jaws may engage bosses on distal ends of the surgical clip. However, the two points of contact do not provide sufficient stability to the surgical clip, which may cause the surgical clip to become misaligned relative to the clip applier during a surgical procedure, or even fall out. The disclosed methods and systems are directed to mitigating or overcoming one or more of the problems set forth above and/or other problems in the prior art.

A first aspect of the present invention is directed to a clip applier configured to apply a surgical clip to tissue. The clip applier may include a first jaw member, a second jaw member, and a stabilizing member, each configured to engage the surgical clip. The stabilizing member may be configured to move longitudinally with respect to the clip applier from a first position at least partially between the first and second jaw members to a second position at least partially between the first and second jaw members. The longitudinal movement of the stabilizing member may be constrained to longitudinal movement between the first and second positions.

In some embodiments, the stabilizing member may include first and second sidewalls on a distal portion, the first and second sidewalls being configured to stabilize the surgical clip in a lateral direction. In some embodiments, the clip applier may include a hinge pin configured to pivotably secure the first and second jaw members, where the stabilizing member may have a longitudinal channel configured to receive the hinge pin, and the hinge pin may be configured to constrain the longitudinal movement of the stabilizing member between the first and second positions. In some embodiments, the stabilizing member may include a tubular portion proximal of the elongate slot and a shaft portion distal of the tubular portion. A width of a distal portion of the stabilizing member may be greater than a width of the shaft portion. In some embodiments, the clip applier may include a spring positioned on a proximal end of the stabilizing member, where the spring is configured to bias the stabilizing member to the first position, and the first position is distal of the second position. In some embodiments, the clip applier may include a shaft secured to proximal ends of the first and second jaw members, the shaft having at least one elongated slot along its length, and the spring being visible through the at least one elongated slot of the shaft. In sonic embodiments, the clip applier may include a tubular member abutting a proximal end of the spring, where a distal portion of the spring abuts a tubular portion on a proximal portion of the stabilizing member. In some embodiments, the stabilizing member may include a plurality of protrusions on the distal portion, the plurality of protrusions being configured to stabilize the surgical clip in a vertical direction. In some embodiments, the first jaw member may be configured to engage a distal portion of a first leg member of the surgical clip, the second jaw member may be configured to engage a distal portion of a second leg member of the surgical clip, and the stabilizing member may be configured to engage a proximal portion of the surgical clip. In sonic embodiments, the first jaw member may be configured to engage a first substantially flat surface on the distal portion of the first leg member, and the second jaw member may be configured to engage a second substantially flat surface on the distal portion of the second leg member.

A second aspect of the present invention is directed to a method of loading a clip applier with a surgical clip. The method may include receiving a proximal portion of the surgical clip between first and second jaw members of the clip applier, and then engaging a stabilizing member with the proximal portion of the surgical clip with the stabilizing member in a first position at least partially between the first and second jaw members. The method may include retracting the stabilizing member to a second position at least partially between the first and second jaw members. The method may further include stabilizing the surgical clip between the stabilizing member and the first and second jaw members.

In some embodiments, the longitudinal movement of the stabilizing member may be constrained to longitudinal movement between the first position and the second position. In some embodiments, stabilizing the surgical clip may include stabilizing the surgical clip in a lateral direction with first and second walls extending from a distal end of the stabilizing member. In some embodiments, stabilizing the surgical clip may include stabilizing the surgical clip in a vertical direction with a plurality of protrusions on a distal surface of the stabilizing member. In some embodiments, the method may include picking the surgical clip up from a cartridge.

A third aspect of the present invention is directed to a stabilizing member for a clip applier. The stabilizing member may include an elongated body having a proximal portion and a distal portion. The stabilizing member may include first and second sidewalls on the distal portion of the elongated body that may be configured to stabilize a proximal portion of a surgical clip in a lateral direction. The stabilizing member may further include a shaft portion of the elongated body extending from the distal portion, where a width of the distal portion including the first and second walls is greater than a width of the shaft portion.

In sonic embodiments, the stabilizing member may further include a longitudinal channel extending through the elongated body. In some embodiments, the shaft portion may have a substantially rectangular cross-section. In some embodiments, the stabilizing member may include a tubular portion of the elongated body forming the proximal portion. In some embodiments, the stabilizing member may include a plurality of protrusions on the distal portion that may be configured to stabilize the proximal portion of the surgical clip in a vertical direction.

BRIEF DESCRIPTION OF THE DRAWINGS

In order that the disclosure may be readily understood, aspects of this disclosure are illustrated by way of examples in the accompanying drawings.

The same or similar reference numbers are used in the drawings and the following detailed description to refer to the same or similar parts.

DETAILED DESCRIPTION

Figure 1:
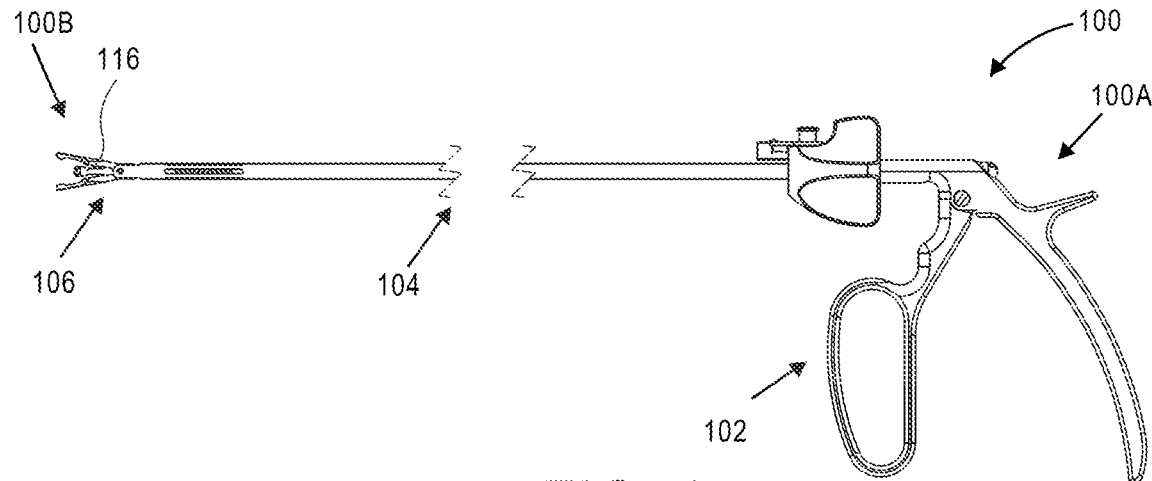
FIG. 1 illustrates a side view of an exemplary clip applier of the present disclosure.

The invention will now be described with reference to the figures, in which like reference numerals refer to like parts throughout, in accordance with conventional practice, as used herein, and unless otherwise indicated herein, the term "proximal portion" refers to the specified portion of a device or its component which is generally closer to the medical personnel handling or manipulating the device as it is intended to be used, and the term "distal portion" shall refer to the specified portion of a device or its component which is opposite of the proximal portion.

The present invention is generally directed to a clip applier configured to increase stability of surgical clips during a medical procedure. The clip applier may include a stabilizing member disposed between first and second jaw members. The stabilizing member and the first and second jaw members may provide at least three points of contact with the surgical clip to prevent relative movement of the surgical clip during the medical procedure. The stabilizing member may have vertical walls extending from a distal portion. The vertical walls may be positioned on opposing sides of a proximal portion of the surgical clip to reduce lateral movement of the surgical clip. A distal portion of the stabilizing member with the vertical walls may have width greater than a shaft extending from the distal portion. The increased width of the distal portion may increase stability of the surgical clip between the jaw members, and prevent retraction of the distal portion through the shaft of the clip applier. The stabilizing member may further have lateral protrusions extending between the vertical walls and being configured to reduce vertical movement.

The stabilizing member may be biased into a first, distal position at least partially between the first and second jaw members to facilitate front-loading of the clip applier. The stabilizing member may engage the surgical clip as it is loaded between the first and second jaw members. The stabilizing member may also retract as the surgical clip is fed between the first and second jaw members to a second, proximal position. The second, proximal position may be at least partially positioned between the first and second jaw members. The stabilizing member may be longitudinally constrained between the first and second positions, for example, through a pin and channel configuration and/or the greater width of the distal portion. The pin may be a pivot pin of the first and second jaw members, and the channel may extend longitudinally through a shall of the stabilizing member. The stabilizing member may move from the first position to the second position and from the second position to the first position, but the stabilizing member cannot move distally of the first position or proximally of the second position. The stabilizing member may therefore be configured to apply a sufficient distal stabilizing force when the surgical clip is received between the first and second jaw members of the clip applier during front-loading of the surgical clip from a cartridge. The clip applier may also be configured hold the surgical clip without any bosses. The clip applier may stabilizing the surgical clip while being applied to tissue (e.g., to ligate blood vessel) preventing the surgical clip from fish-tailing, FIGS. 1-4 illustrate a clip applier 100 configured to apply a surgical clip 200 according to the present disclosure. The clip applier 100 may include a proximal portion 100A and a distal portion 100B. The clip applier 100 may further include a handle mechanism 102, a shaft 104, and a jaw structure 106. The jaw structure 106 may be pivotally connected to the shaft 104 and actuated by the handle mechanism 102.

The jaw structure 106 may include a first jaw member 108 and a second jaw member 110 pivotally coupled at a hinge mechanism 112 having a pivot pin 114. The jaw structure 106 may receive the surgical clip 200 between the first and second jaw members 108, 110, and the first and second jaw members 108, 110 may stabilize the surgical clip 200 at points of contact on distal portions of first and second leg members 202, 204. The jaw members 108, 110 may have engaging surfaces 111 at distal portions. The engaging surfaces 111 may be substantially flat and/or hook shaped and may be configured to releasably engage distal portions of leg members 202, 204 of the surgical clip 200 without bosses.

Figure 4:
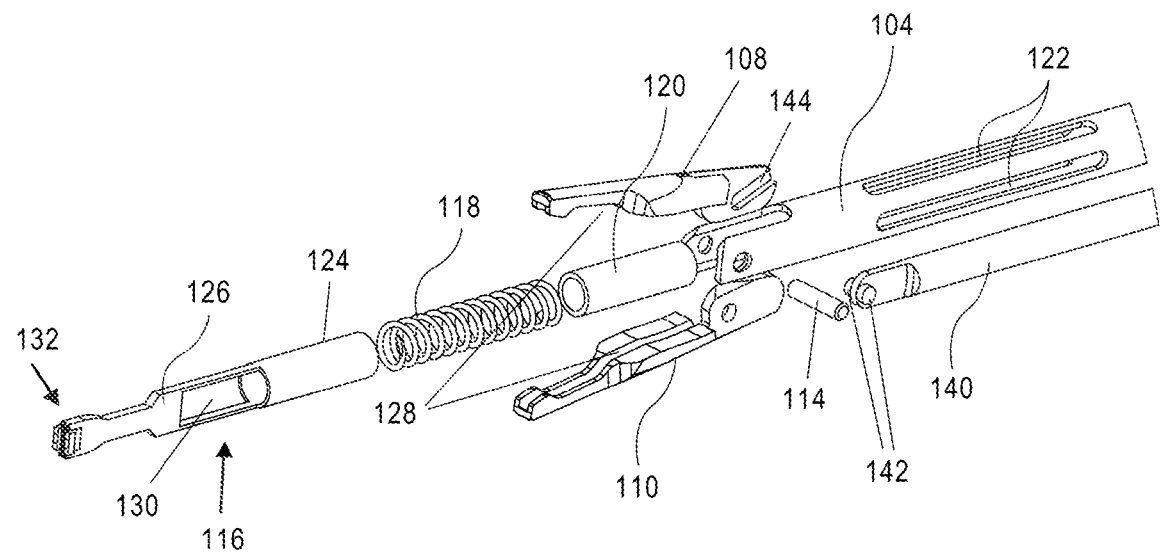
FIG. 4 illustrates an exploded view of the exemplary distal portion of the exemplary clip applier of FIGS. 1-3.

The jaw structure 106 may also be configured to compress the surgical clip 200 by applying opposing forces on the first and second leg members 202, 204, The jaw structure 106 may be actuated by an actuator 140 advanced and retracted by the handle mechanism 102, as illustrated in FIG. 4. The actuator 140 may have projections 142 on a distal portion configured to be received within linear, angled slots 144 on proximal portions of each of the first and second jaw members 108, 110, The actuator 140 may open the jaw structure 106 when the projections 142 are in a proximal position within the slots 144, and the actuator 140 may close the jaw structure 106 when the projections are in a distal position within the slots 144. The actuator 140 may be biased into the proximal position to open the jaw members 108, 110.

The clip applier 100 may further include a stabilizing member 116 configured to be received between the first and second jaw members 108, 110 and to provide additional stability to the surgical clip 200. The stabilizing member 116 may be spring-loaded to apply a distal force on a proximal portion of the surgical clip 200, pushing the surgical clip 200 against the first and second jaw members 108, 110. The stabilizing member 116 may be configured to move longitudinally between a first, distal position at least partially between the first and second jaw members 108, 110 and a second, proximal position at least partially between the first and second jaw members 108, 110. The stabilizing member 116 may be constrained to longitudinal movement between the first and second positions to ensure that suitable pressure is applied by the stabilizing member 116 to the surgical clip 200. The stabilizing member 116 may be positioned symmetrically between the first and second jaw members 108, 110. The positioning of the stabilizing member 116 may allow a user to pick up the surgical clip 200 from a cartridge 400 with the clip applier 100 in either of two opposite orientations. For example, the first jaw member 108 may engage with either of the first leg member 202 or the second leg member 204 of the surgical clip 200, while the second jaw member 110 engages with the other of the first leg member 202 and the second leg member 204. The clip applier 100 may also pick up the surgical clip 200 without bosses, rather the surgical clip 200 may be engaged between the stabilizing member 116 and the engaging surfaces 111.

Figure 2:
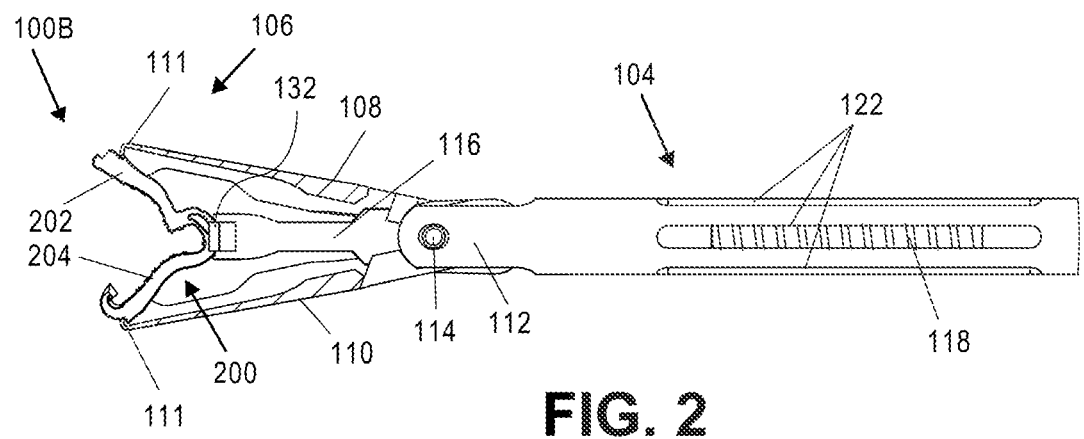
FIG. 2 illustrates a side view of an exemplary distal portion of the exemplary clip applier of FIG. 1 loaded with an exemplary surgical clip.
Figure 3:
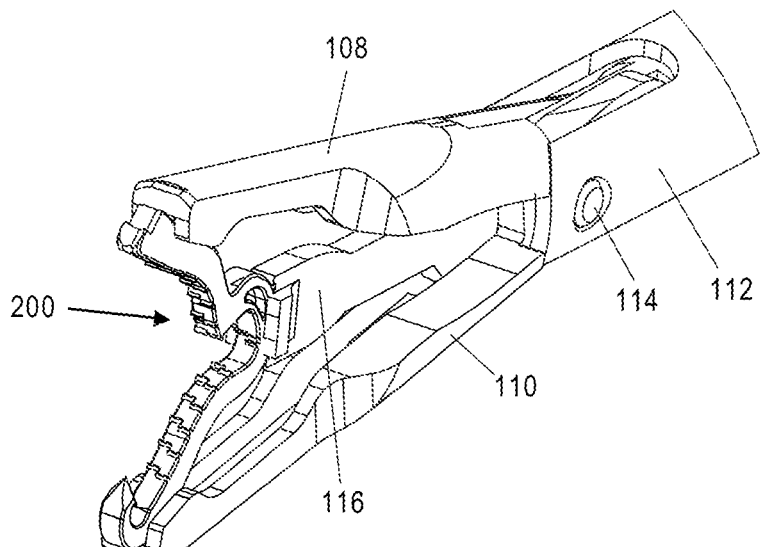
FIG. 3 illustrates a perspective view of the exemplary distal portion of the exemplary clip applier of FIGS. 1 and 2.

The stabilizing member 116 may be biased distally by a spring member 118 disposed between the stabilizing member 116 and a tubular member 120. The spring member 118 may be compressed as the stabilizing member 116 is retracted when the surgical clip 200 is received within the first and second jaw members 108, 110. The spring member 118 may provide a distal force to the stabilizing member 116 to engage the surgical clip 200. The spring member 118 may also be further compressed as the surgical clip 200 is compressed, allowing lengthening of the leg members 202, 204 when latching in a closed configuration. As depicted in FIGS. 2, 4, internal components (e.g., the spring member 118) may be exposed and/or visible through elongated slots 122 extending through the shaft 104. The elongated slots 122 may allow for inspection, cleaning, and/or flushing of the internal components without disassembly of the clip applier 100. The actuator 140 may extend through the shaft 104, the tubular member 120, and the spring member 118 to engage the slots 144 of each of the first and second jaw members 108, 110.

Figure 5:
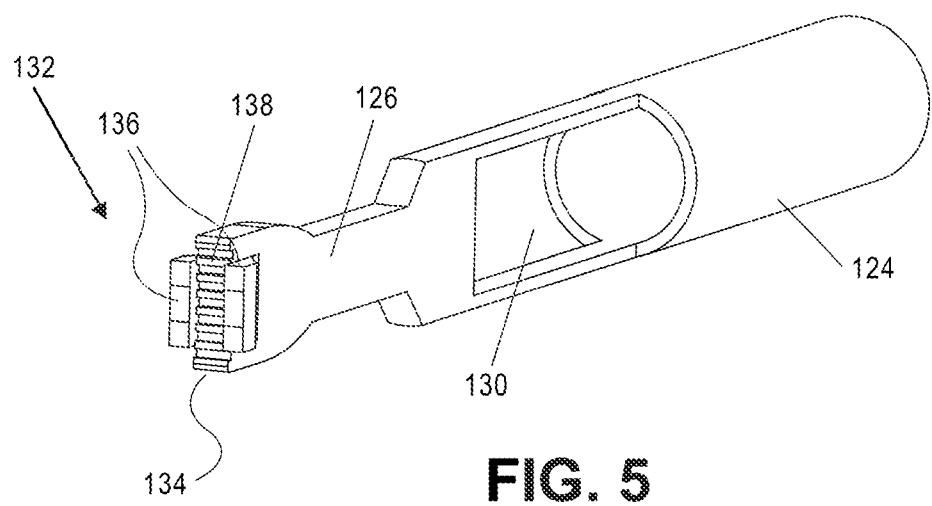
FIG. 5 illustrates a perspective view of an exemplary stabilizing member of the exemplary clip applier of FIGS. 1-4.

As further depicted in FIGS. 4-5, the stabilizing member 116 may include an elongated body having a tubular portion 124 on and forming a proximal portion and a shaft portion 126 distal of the tubular portion 124. The tubular portion 124 may be received in the shaft 104 and have a proximal end that abuts the spring member 118. The tubular portion 124 may have a lumen configured to receive the actuator 140. The shaft portion 126 may have a substantially rectangular cross-section having substantially flat side surfaces configured to be received through longitudinal slot 128 on inner surfaces of the first and second jaw members 108, 110. The shaft portion 126 may therefore extend into an opening between the first and second jaw members 108, 110. A distal face 132 distal of the shaft portion 126 may engage the proximal portion (e.g., a hinge portion 206) of the surgical clip 200. The distal face 132 may be on a distal portion of the stabilizing member 116 and have a width greater than a width of the longitudinal slot 128, preventing retraction of the distal face 132 past the second position and passage through the first and second jaw members 108, 110.

The shaft portion 126 may have a longitudinal channel 130 that receives the pivot pin 114. The interaction between the pivot pin 114 and the longitudinal channel 130 may constrain the longitudinal movement of the stabilizing member 116 to longitudinal movement between the first and second positions. For example, the pivot pin 114 may contact a proximal surface of the longitudinal channel 130 when the stabilizing member 116 is in the first, distal position, and the pivot pin 114 may contact a distal surface of the longitudinal channel 130 when the stabilizing member 116 is in the second, proximal position. The pivot pin 114 may also prevent rotation of the stabilizing member 116. The longitudinal channel 130 may be in communication with the lumen of the tubular portion 124. The shaft portion 126 may have a neck region with a height less than a height of proximal and distal portions of the shaft portion 126.

As further depicted in FIG. 5, the distal face 132 may have a distal surface 134 with lateral protrusions 138 configured to engage with the proximal portion of the surgical clip 200. The distal surface 134 may grip the surgical clip 200 and/or stabilize the surgical clip 200 in a vertical direction when positioned between the first and second jaw members 108, 110. The distal face 132 may include vertical walls 136 extending on opposing sides of the stabilizing member 116. The vertical walls 136 may define a cavity therebetween configured to receive the proximal portion of the surgical clip 200, reducing lateral movement of the surgical clip 200. The distal face 132 including the vertical walls 136 may have a width greater than the shaft portion 126 and the longitudinal slot 128 of the first and second jaw members 108, 110, preventing retraction of the distal face 132 through the first and second jaw members 108, 110. The vertical walls 136 may be substantially parallel, and the protrusions 138 may extend therebetween. The vertical walls 136 may each have a substantially flat distal surface and a tapered proximal surface joining the shaft portion 126. The vertical walls 136 may not extend the entire height of the distal surface 134.

Figure 6:
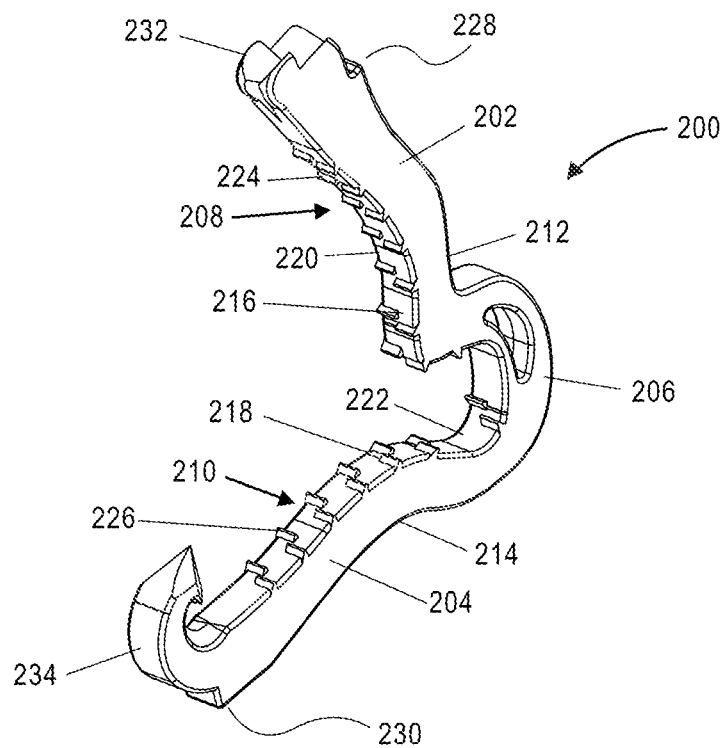
FIG. 6 illustrates a perspective view of a first exemplary embodiment of a surgical clip that may be applied with the exemplary clip applier of FIGS. 1-5.

FIG. 6 illustrates the surgical clip 200 according to a first embodiment of the disclosure. The surgical clip 200 may include the first leg member 202 and the second leg member 204 joined at the hinge portion 206. Each of the first and second leg members 202, 204 may include an inner surface 208, 210 and an outer surface 212, 214. Each of the inner surfaces 208, 210 may include a convex portion 216, 218 and a concave portion 220, 222, the concave portions 220, 222 being configured to receive the convex portions 216, 218 in a closed and/or latched configuration. The convex portions 216, 218 may be configured to pinch tissue proximate the hinge portion 206 prior to full closure of the surgical clip 200, to allow manipulation and/or retraction of the tissue. Each of the inner surfaces 208, 210 may further include a plurality of teeth 224, 226 configured to further secure the tissue between the first and second leg members 202, 204.

Each of the first and second leg members 202, 204 may also include an engaging surface 228, 230 configured to engage the first and second jaw members 108, 110 of the clip applier 100. As depicted in FIG. 6, the engaging surfaces 228, 230 may include substantially flat, distally-facing surfaces, formed on the outer surfaces 212, 214 of the first and second leg members 202, 204. The engaging surfaces 228, 230 may be configured to engage the engaging surfaces 111 of the jaw members 108, 110 when secured in the clip applier 100. Therefore, the surgical clip 200 may be secured by the clip applier 100 without any circularly, round and/or laterally protruding bosses. The clip applier 100 does not require the bosses at the distal end of the surgical clip 200, due to positive locking of the surgical clip 200 caused by the distal force applied by the stabilizing member 116. Eliminating the bosses on the surgical clip 200 reduces the vertical and/or lateral profile of the surgical clip 200, reducing the space needed and/or trauma caused by the surgical clip 200.

The first leg member 202 may include a tip member 232, and the second leg member 204 may include a hook member 234. As the surgical clip 200 is closed, the hook member 234 may deflect around the tip member 232 to secure the surgical clip 200 in a latched configuration. The first and/or second leg members 202, 204 may straighten and/or elongate during the latching process. The engaging surface 228 of the first leg member 202 may be positioned immediately proximal of the tip member 232, and the engaging surface 230 of the second leg member 204 may be positioned immediately proximal of the hook member 234.

Figure 7:
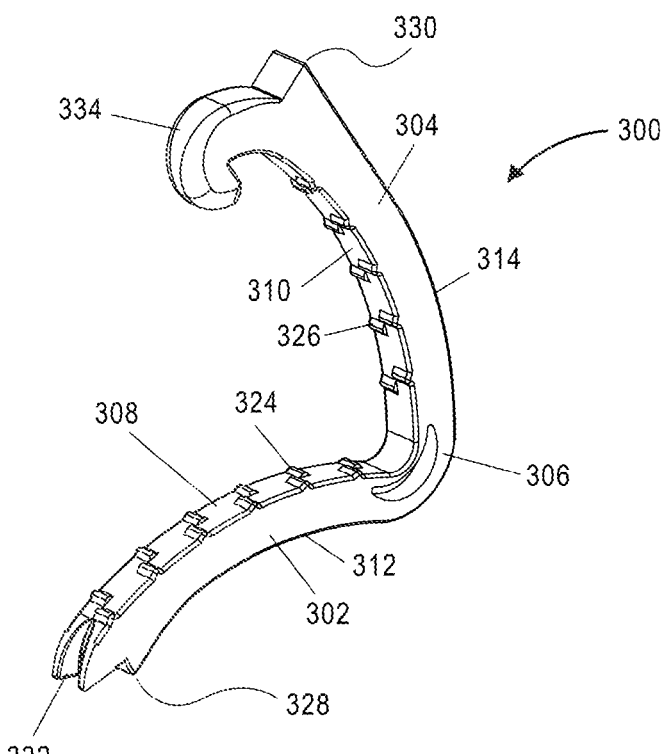
FIG. 7 illustrates a perspective view of a second exemplary embodiment of a surgical clip that may be applied with the exemplary clip applier of FIGS. 1-5.

FIG. 7 illustrates a surgical clip 300 according to a second embodiment of the disclosure. The surgical clip 300 may include a first leg member 302 and a second leg member 304 joined at a hinge portion 306. The first leg member 302 may have an inner surface 308 with a convex curvature, and the second leg member 304 may have an inner surface 210 with a concave curvature. The concave curvature of the second leg member 304 may be configured to receive the convex curvature of the first leg member 302 in a latched and/or closed configuration. Each of the inner surfaces 308, 310 may further include a plurality of teeth 324, 326 configured to further secure the tissue between the first and second leg members 302, 304.

Each of the first and second leg members 302, 304 may also include an engaging surface 328, 330 configured to engage the first and second jaw members 108, 110 of the clip applier 100. As depicted in FIG. 6, the engaging surfaces 328, 330 may include substantially flat, distally-facing surfaces, formed on the outer surfaces 312, 314 of the first and second leg members 302, 304. The engaging surfaces 328, 330 may be configured to engage the engaging surfaces ill of the jaw members 108, 110 when secured in the clip applier 100. Therefore, the surgical clip 200 may be secured by the clip applier 100 without any bosses, as further discussed above.

The first leg member 302 may include a tip member 332, and the second leg member 304 may include a hook member 334. As the surgical clip 300 is closed, the hook member 334 may deflect around the tip member 332 to secure the surgical clip 300 in a latched configuration. The first and/or second leg members 302, 304 may straighten and/or elongate during the latching process. The engaging surface 328 of the first leg member 302 may be positioned immediately proximal of the tip member 332, and the engaging surface 330 of the second leg member 304 may be positioned immediately proximal of the hook member 334.

Figure 8A:
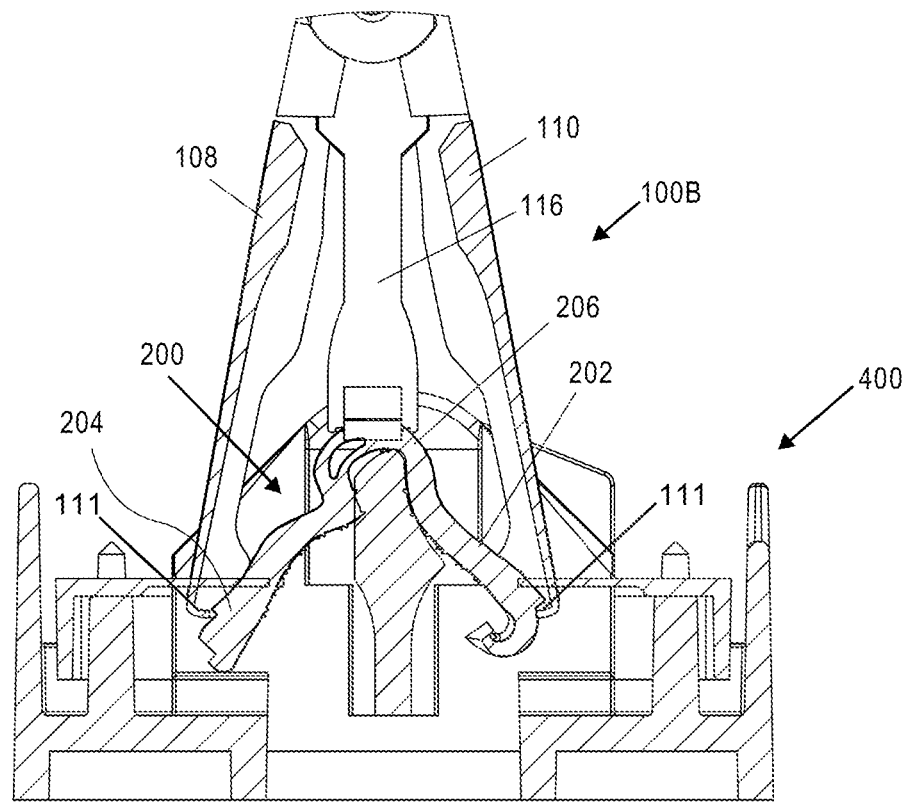
FIGS. 8A-B illustrate an exemplary method of loading an exemplary clip into the exemplary clip applier of FIGS. 1-5.
Figure 8B:
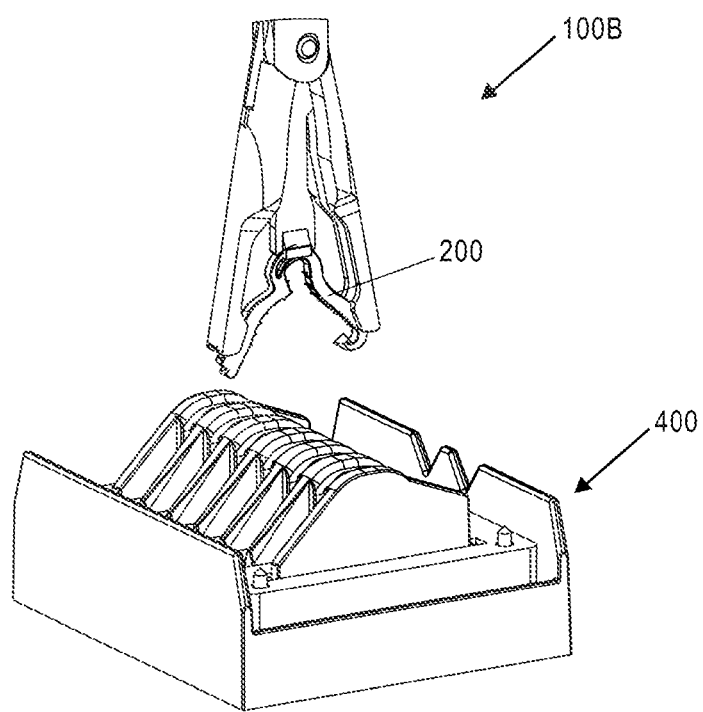

FIGS. 8A-B illustrate the clip applier 100 being loaded with the surgical clip 200 from a cartridge 400. FIG. 8A illustrates a cutaway view of the clip applier 100 as it engages the surgical clip 200 positioned in the cartridge 400, and FIG. 8B illustrates an isometric view of the clip applier 100 shortly after removing the surgical clip 200 from the cartridge 400. As shown, the three point engagement between the clip applier 100 and the surgical clip 200 increases the security of the surgical clip 200. Two points of contact occur on the surgical clip 200 at distal surfaces of the first and second leg members 202, 204, and a third point of contact occurs at a proximal portion of the surgical clip 200 (e.g., the hinge portion 206). Compression of the spring member 118 may provide a distal force by the stabilizing member 116 as the surgical clip 200 is picked up, such that the surgical clip 200 remains positively engaged between the stabilizing member 116 and the engaging surfaces 111 of the first and second jaw members 108, 110, despite external forces. Only when the clip applier 100 fully closes and/or latches the surgical clip 200, does the surgical clip 200 become free of the engaging surfaces 11 of the first and second jaw members 108, 110. The first and second jaw members 108, 110 may then be opened and removed to leave the surgical clip 200 in place. Although FIGS. 2, 3, and 8A-B illustrate the clip applier 100 loaded with the surgical clip 200, it should be readily understood that the clip applier 100 may be used with the surgical clip 300.

The various embodiments of the surgical clips 200, 300 of the present invention may be made of any suitable size and may be applied to any number of tissues, such as blood vessels, lymph nodes, nerves, fallopian tubes, or cardiac tissue. The various embodiments of the surgical clips 200, 300 may be constructed from any suitable biocompatible material, such as metals and polymers. However, the present invention is particularly suitable for practice with polymeric clips. Thus, the various embodiments of the surgical clips 200, 300 preferably consist of a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded, or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip to tissue, the clip applier comprising:
    first and second jaw members configured to engage the surgical clip;
    a pin pivotably connecting the first and second jaw members; and
    a stabilizing member including a shaft portion having a channel, the stabilizing member having a distal portion configured to engage the surgical clip, and the stabilizing member being configured to move longitudinally with respect to the clip applier from a first position at least partially between the first and second jaw members to a second position at least partially between the first and second jaw members,
    wherein the pin is received in the channel to stabilize the stabilizing member, and constrain longitudinal movement of the stabilizing member to longitudinal movement between the first and second positions, and wherein the stabilizing member is configured to prevent or reduce lateral movement of the surgical clip relative to the clip applier and/or prevent or reduce vertical movement of the surgical clip relative to the clip applier.

2. The clip applier of claim 1, wherein the pin engages an end of the channel when the stabilizing member is in the first position to constrain the longitudinal movement of the stabilizing member.

3. The clip applier of claim 2, wherein the pin engages a second end of the channel when the stabilizing member is in the second position to constrain the longitudinal movement of the stabilizing member.

4. The clip applier of claim 2, wherein the first position is distal of the second position.

5. The clip applier of claim 1, wherein the channel is in the stabilizing member.

6. The clip applier of claim 5, wherein the channel extends longitudinally along the stabilizing member.

7. The clip applier of claim 1, wherein each of the first and second jaw members have a slot on an inner surface, and the stabilizing member is configured to be received in the slots of the first and second jaw members.

8. The clip applier of claim 1, wherein a width of a distal portion of the stabilizing member is greater than a width of the shaft portion.

9. The clip applier of claim 8, wherein the shaft portion has a substantially rectangular cross-section.

10. The clip applier of claim 1, further comprising a spring positioned on a proximal portion of the stabilizing member, the spring is configured to bias the stabilizing member to the first position, and the first position is distal of the second position.

11. The clip applier of claim 1, wherein the first jaw member is configured to engage a distal portion of a first leg member of the surgical clip, the second jaw member is configured to engage a distal portion of a second leg member of the surgical clip, and the stabilizing member is configured to engage a proximal portion of the surgical clip.

12. The clip applier of claim 11, wherein the first jaw member is configured to engage a first substantially flat surface on the distal portion of the first leg member, and the second jaw member is configured to engage a second substantially flat surface on the distal portion of the second leg member.

13. The clip applier of claim 1, wherein the stabilizing member has first and second sidewalls on laterally opposite sides of the shaft portion, the first and second sidewalls extending vertically between the first and second jaw members and being configured to receive the surgical clip therebetween and be positioned on laterally opposite sides of the surgical clip to stabilize the surgical clip in a lateral direction.

14. The clip applier of claim 1, wherein the pin pivotably secures the first and second jaw members.

15. The clip applier of claim 1, wherein the pin extends laterally through the shaft.

16. The clip applier of claim 1, wherein the pin is configured to contact a proximal surface of the channel when the stabilizing member is in the first position, and the pin is configured to contact a distal surface of the channel when the stabilizing member is in the second position.

17. The clip applier of claim 1, further comprising an actuator configured to move the first and second jaw members from the first position to the second position.

18. The clip applier of claim 17, wherein the actuator includes a distal portion having a first projection and a second projection.

19. The clip applier of claim 18, wherein the first projection is configured to engage a proximal portion of the first jaw member, and the second projection is configured to engage a proximal portion of the second jaw member.

* * * * *